US00PP11906P2

(12) United States Plant Patent

VandenBerg

(10) Patent No.: US PP11,906 P2

(45) Date of Patent: Jun. 5, 2001

(54) CHRYSANTHEMUM PLANT NAMED 'FALL DELANO'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/270,787

(22) Filed: Mar. 17, 1999

(51) Int. Cl.[7] ..... A01H 5/00

(52) U.S. Cl. ..... Plt./287

(58) Field of Search ..... Plt./287, 289, 290, Plt./292, 293

(56) References Cited

U.S. PATENT DOCUMENTS

P.P. 8,345 * 8/1993 VandenBerg ..... Plt./293
P.P. 9,843 * 4/1997 Van Koeveringe ..... Plt./287

OTHER PUBLICATIONS

Broertjes, et al., 1978, "Application of Mutation Breeding Methods in the Improvement of Vegetatively Propagated Crops", Elsevier Sci. Pub. Co., New York, pp. 162–175.*

Gupta, et al., 1978, "Mutation breeding of chrysanthemum. II Detection of gamma ray induced mutations in uM2", J. Nuclear Agric. Biol. 7(2): 50–54.*

Glazurina, et al., 1977, "Use of the method of artificial mutagenesis in the breeding of flower crops", Cytology and Genetics, vol. 11(3): 42–45.*

Das, et al., 1977, "Improvement of some vegetatively propagated ornamentals by gamma radiation", Indian. J. Horticulture, 34(2):169–174.*

"Mutation studies on chrysanthemum", NBRI Newsletter, 1989, 16(1):2–3.*

Datta, 1991, "Evaluation of recurrent irradiation on vegetatively propagated ornamentals: Chrysanthemum", J. Nuclear Agric. Biol., 20(2):81–86.*

Banerji, et al., 1990, "Induction of somatic mutation in chrysanthemum cultivar 'Anupam'", J. Nuclear Agric. Biol., 19:252–256.*

Gosling, ed., 1979, "The Chrysanthemum Manual—6$^{th}$ edition", The National Chrysanthemum Society, Essex Telegraph Press, Ltd., London, pp. 329–336.*

Searle, et al., 1968, "Chrysanthemums the Year Round", Blanford Press, London, pp. 27–29, 320–327.

Dowrick, et al., 1966, "The induction of mutations in chrysanthemum using X– and gamma radiation", Euphytica, 15:204–210.

Broertjes, 1966, "Mutation breeding of chrysanthemums", Euphytica, 15:156–162.

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Fall Delano', characterized by its upright and uniformly mounded plant habit; freely branching habit; strong plant growth; large and very dark green leaves; uniform flowering; large decorative disbud-type inflorescences that are about 11.9 cm in diameter; attractive dulled red ray florets; with cool temperatures and low light conditions, ray floret color can range from a yellow ray base with reddish bronze apices to yellow; and good postproduction longevity with inflorescences and leaves maintaining good substance and color for about three weeks in an interior environment.

4 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Fall Delano.

The new Chrysanthemum is a product of a mutation induction breeding program conducted by the Inventor in Fort Myers, Fla., and Salinas, Calif. The objective of the program is to create new Chrysanthemum cultivars with desirable inflorescence form and floret colors, and moderate plant post-production longevity.

The new Chrysanthemum originated by exposing unrooted cuttings of the Chrysanthemum cultivar Spring Delano, disclosed in U.S. Plant Pat. No. 9,843, to gamma radiation in September, 1993, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the inventor as a single flowering plant within this population in March, 1994. The selection of this plant was based on its desirable inflorescence form and floret colors and good post-production longevity.

Asexual reproduction of the new Chrysanthemum by terminal cuttings harvested in a controlled environment in Fort Myers, Fla., has shown that the unique features of this new Chrysanthemum are stable and reproduced true in successive generations.

SUMMARY OF THE INVENTION

The cultivar Fall Delano has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Fall Delano'. These characteristics in combination distinguish 'Fall Delano' as an new and distinct Chrysanthemum:

1. Upright and uniformly mounded plant habit.
2. Freely branching habit.
3. Strong plant growth.
4. Large and very dark green leaves.
5. Uniform flowering.
6. Large decorative disbud-type inflorescences that are about 11.9 cm in diameter.
7. Attractive dulled red ray florets; when grown under cooler, low light conditions, ray floret color can range from a yellow ray base with reddish bronze apices to yellow occasionally with bronze flecking.
8. Good postproduction longevity with inflorescences and leaves maintaining good substance and color for about three weeks in an interior environment.

Plants of the new Chrysanthemum can be compared to plants of the parent cultivar Spring Delano. However, in side-by-side comparisons conducted by the Inventor under commercial practice in Salinas, Calif., plants of the new Chrysanthemum differed from plants of the cultivar Spring Delano in the following characteristics:

1. Plants of the new Chrysanthemum flowers about 2 to 5 days later than plants of the cultivar Spring Delano.
2. Plants of the new Chrysanthemum do not flower as uniformly as plants of the cultivar Spring Delano.
3. Plants of the new Chrysanthemum have fewer ray florets per inflorescence than plants of the cultivar Spring Delano.
4. Ray floret color of plants of the new Chrysanthemum is dull red whereas ray floret color of plants of Spring Delano is reddish purple.

The new Chrysanthemum can be compared to the Chrysanthemum cultivar Red Delano, disclosed in U.S. Plant Pat. No. 8,345 a radiation induced mutation of the cultivar Delano, disclosed in U.S. Plant Pat. No. 6,950. However in side-by side comparsions in Salinas, Calif., and Leamington, Ontario, Canada, under commerical practice, plants of the new Chrysanthemum differed from plants of the cultivar Red Delano in the following characteristics:

1. Plants of the new Chrysanthemum flowers about 2 to 5 days later than plants of the cultivar Red Delano.
2. Plants of the new Chrysanthemum do not flower as uniformly as plants of the cultivar Red Delano.
3. Plants of the new Chrysanthemum have fewer ray florets per inflorescence than plants of the cultivar Red Delano.
4. When grown under warm, high light conditions, ray floret color of new Chrysanthemum is dulled red whereas ray floret color of the cultivar Red Delano is darker and richer red.
5. When grown under cool, low light conditions, ray floret color of new Chrysanthemum will be bronze to yellow whereas dark red ray floret color of the cultivar Red Delano is maintained.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph on the first sheet comprises a side perspective view of a typical flowering plant of 'Fall Delano'.

The photograph at the top of the second sheet comprises a close-up view of upper (left) and lower (right) surfaces of typical inflorescences.

The photograph at the bottom of the second sheet comprises a close-up view of upper (left) and lower (right) surfaces of typical leaves of the cultivar Fall Delano.

The photograph at the top of the third sheet comprises a side perspective view of typical flowering plants of 'Fall Delano' (left) and 'Red Delano' (right).

The photograph at the bottom of the third sheet comprises a close-up view of upper surfaces of typical inflorescences of plants of 'Fall Delano' (left) and 'Red Delano' (right).

The photographs on the fourth sheet comprises close-up views of typical inflorescences of plants grown under cool and low light conditions (top); warmer and higher light conditions (middle) and warm and high light conditions (bottom). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary signficance are used. The following observations and measurements describe plants grown in Salinas, Calf., and Leamington, Ontario, Canada, under greenhouse conditions which approximate those generally used in commercial potted Chrysanthemum production. Four unrooted cuttings were directly stuck in a 15-cm container and pinched once. Plants used for this description were grown under warm and high light conditions. Measurements and numberical values represent averages of typical flowering plants.

Botanical classification: *Dendranthema grandifora* cultivar Fall Delano.

Commercial classification: Decorative disbud-type pot Chrysanthemum.

Parentage: Induced mutation of *Dendranthema grandifora* cultivar Spring Delano, disclosed in U.S. Plant No. 9,843.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative disbud-type pot Chrysanthemum. Inverted triangle; stems mostly upright; uniformly mounded appearance to the plant. Freely branching; about four lateral branches develop after removal of terminal apex (pinching); dense and full plants.

*Plant height.*—About 39 cm.

*Plant width.*—About 45 cm.

*Stem color.*—Close to 147A.

*Stem texture.*—Pubescent.

*Foliage description.*—Arrangement: Alternate. Length: About 10.6 cm. Width: About 7.5 cm. Apex: Mucronate. Base: Attenuate. Margin: Palmately lobed, sinuses between lateral lobes mostly parallel. Texture: Upper and lower surfaces with very fine pubescence; veins prominent on lower surface; somewhat glossy. Petiole length: About 2.5 cm. Color: Young foliage upper surface: Darker than 147A. Young foliage lower surface: Mature foliage upper surface: Darker than 147A. Mature foliage lower surface: Close to 147A. Close to 147A. Venation upper surface: 147B. Venation lower surface: 147B.

Inflorescence description:

*Appearance.*—Decorative disbud-type inflorescence form with broad oblong-shaped ray florets. Inforescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 8 to 8.5 weeks later.

*Postproduction longevity.*—Inflorescences and leaves will maintain good color and substance for about three weeks in an interior environment.

*Quantity of Inflorescences.*—As a disbud-type, all lateral inflorescences are removed to allow for maximum terminal inflorescence size. One inflorescence per lateral stem; about four inflorescences per plant.

*Inflorescence bud.*—Height: About 6 mm. Diameter: About 1 cm. Color: Close to 147A.

*Inflorescence size.*—Diameter: About 11.9 cm. Depth (height): About 3.9 cm. Diameter of disc: About 5 mm, inconspicuous.

*Ray florets.*—Shape: Oblong with short corolla tube. Orientation: Mostly incurved and upright; outer florets perpendicular to peduncle. Aspect: Mostly concave. Length: About 6.5 cm. Width: About 2.2 cm. Apex: Acute to emarginate. Margin: Entire. Texture: Smooth, glabrous. Number of ray florets per inflorescence: About 198. Color: When opening: 183C to 183D to 184C. Fully opened, upper surface: When plants of the new Chrysanthemum are grown under warm temperatures and high light conditions, ray florets will be dulled red, 182A overlaid with 185A. When plants of the new Chrysanthemum are grown under cool temperatures and low light conditions, ray florets will be bronze, 179A to 180A, to yellow, 9A, overlaid with bronze, 179A, to 180A, to yellow, 9A, occasionally with bronze flecking. Fully opened, lower surface: When plants of the new Chrysanthemum are grown under warm temperatures and high light conditions, base of ray florets will be light tan; mid-section and apex, tan overlaid with 182A to 182B. When plants of the new Chrysanthemum are grown under cool temperatures and low light conditions, ray florets will be yellow, 8A to 8B, overlaid with close to 181B to 181C.

*Disc florets.*—Shape: Tubular. Apex: Serrated. Length: About 6 mm. Width: Apex: About 1.5 mm. Base: About 1 mm. Number of disc florets per inflorescence: Few, about 18. Color: Immature: Greener than 154A. Mature: Apex: 9A. Base: White, 155D.

*Reproductive organs.*—Androecium: Present on disc florets only. Anther color: 13A. Pollen: Amount: Very scarce. Color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Fall Delano', as illustrated and described.

* * * * *

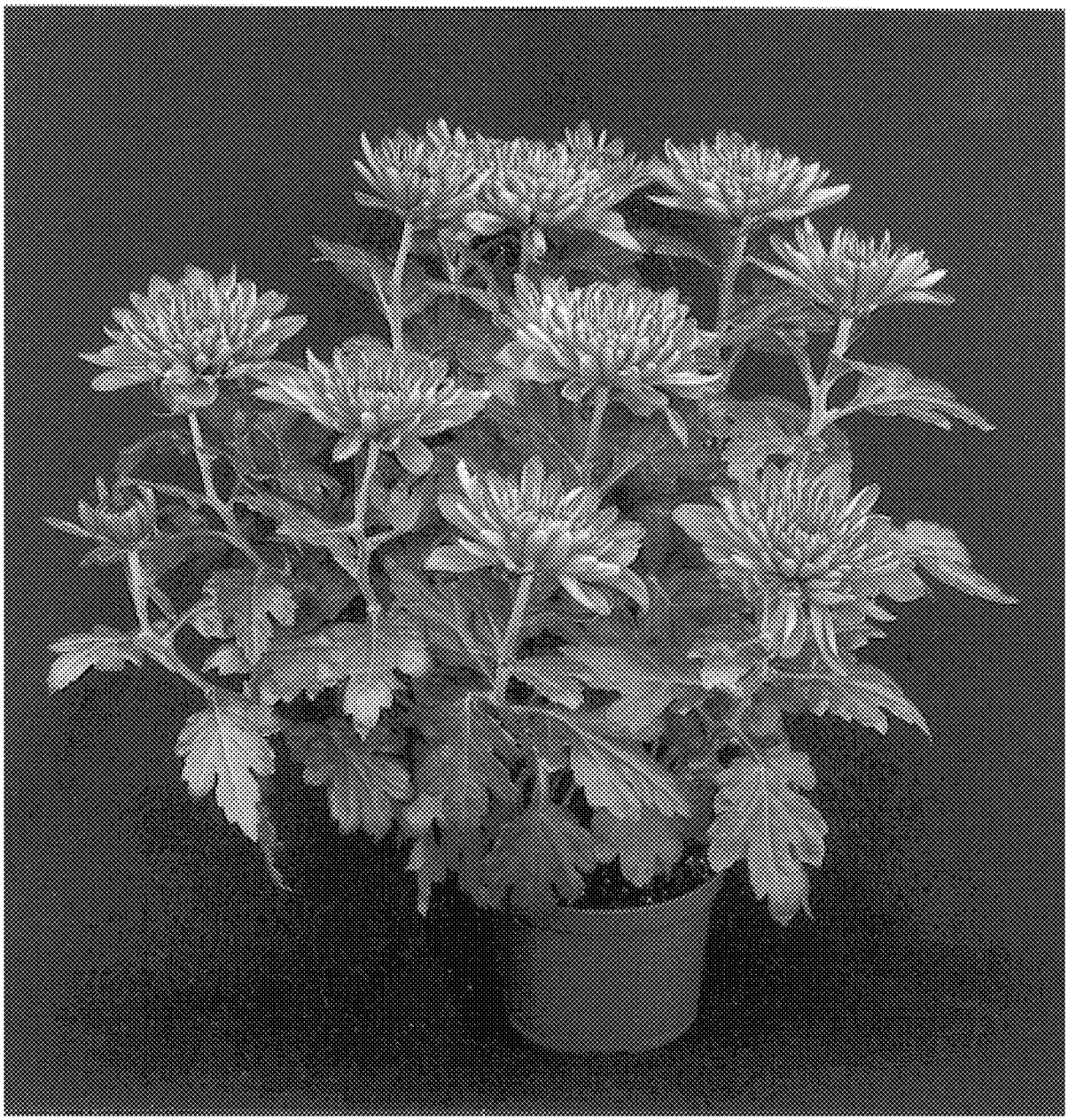

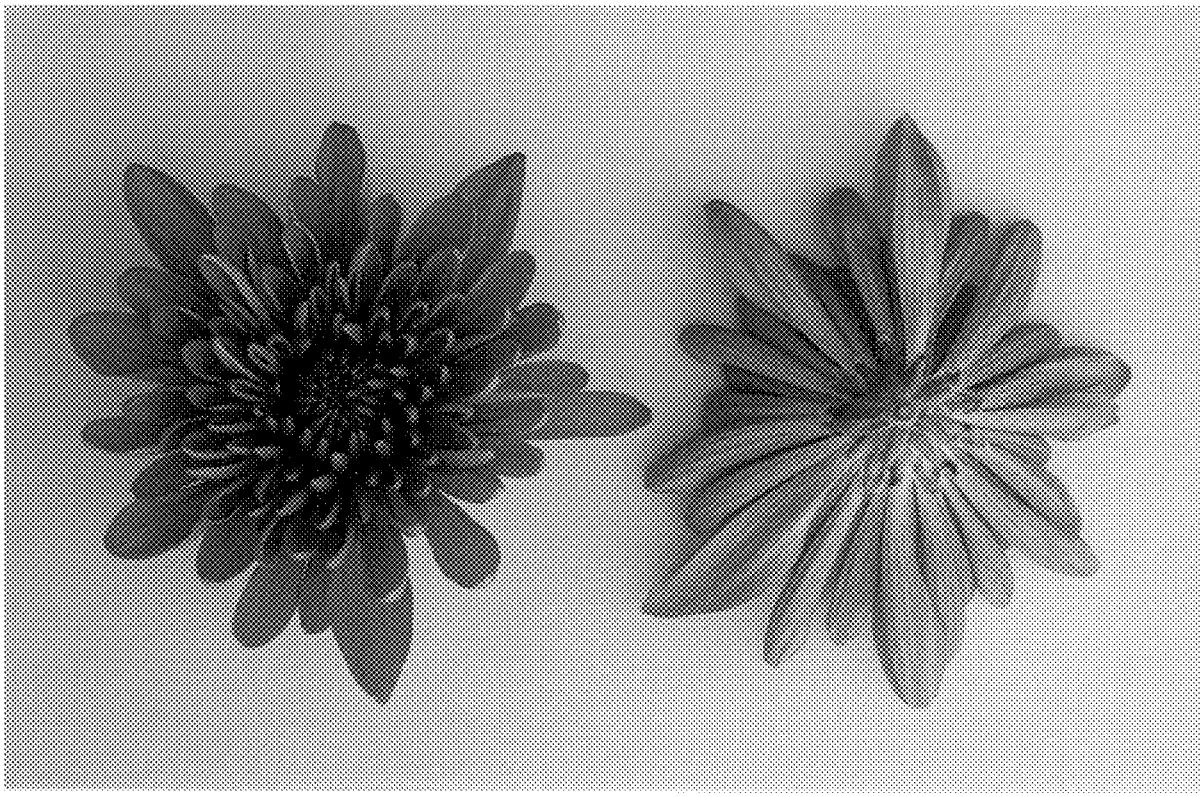
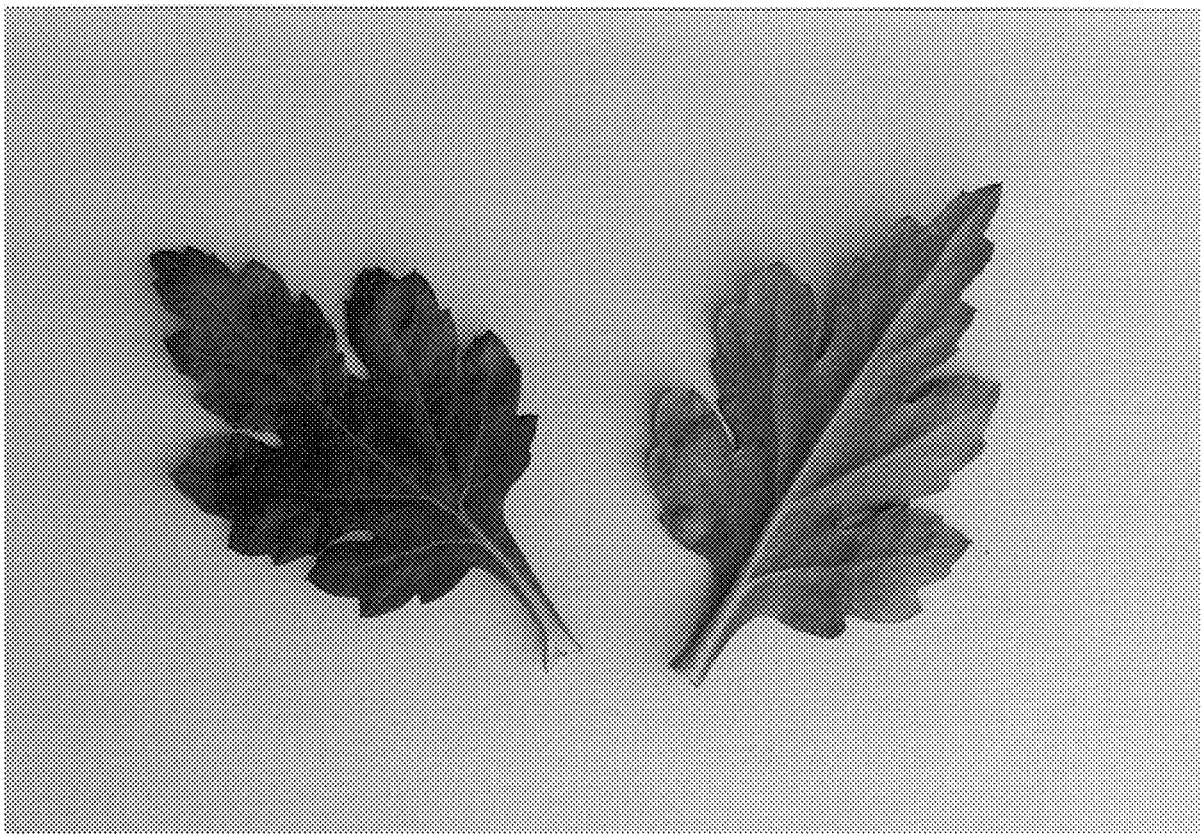

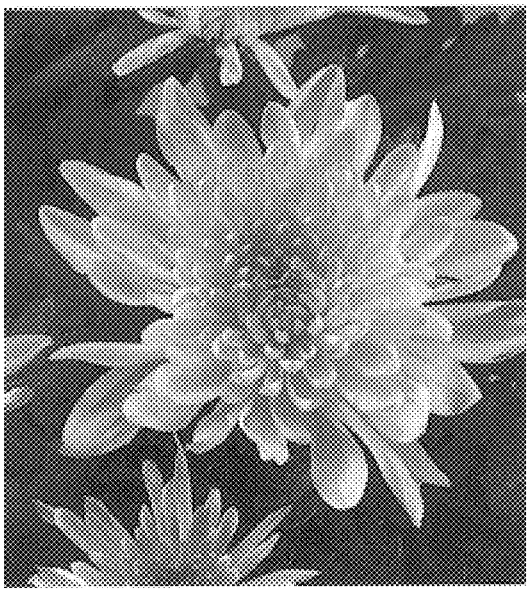
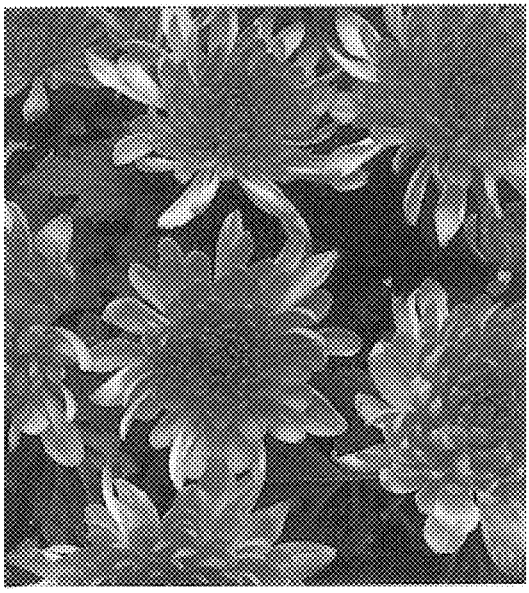
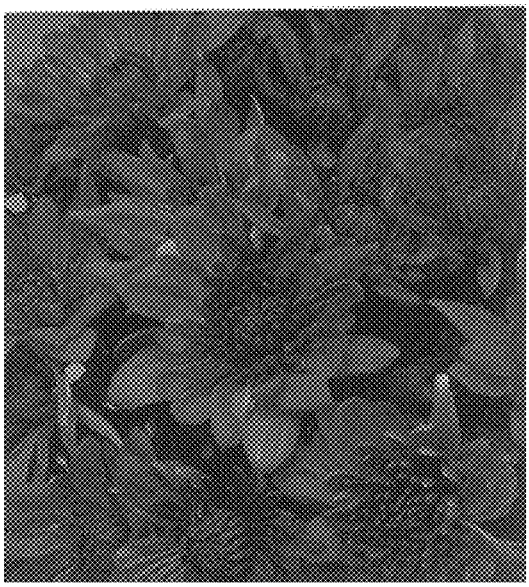

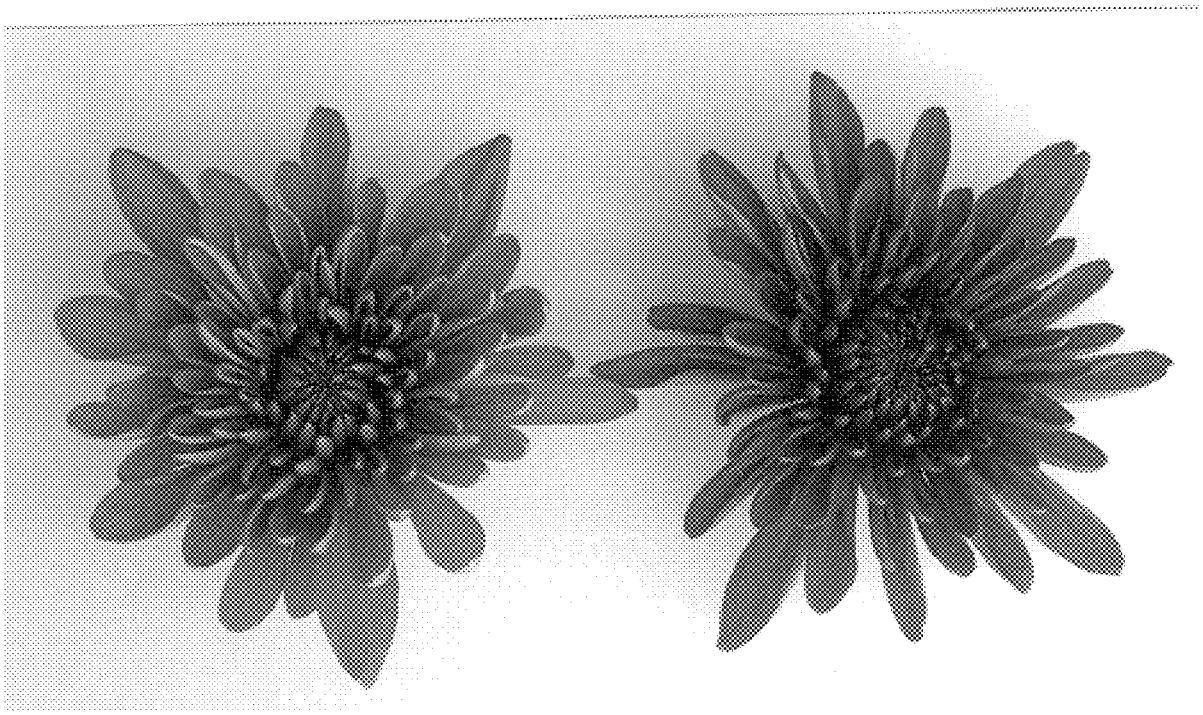

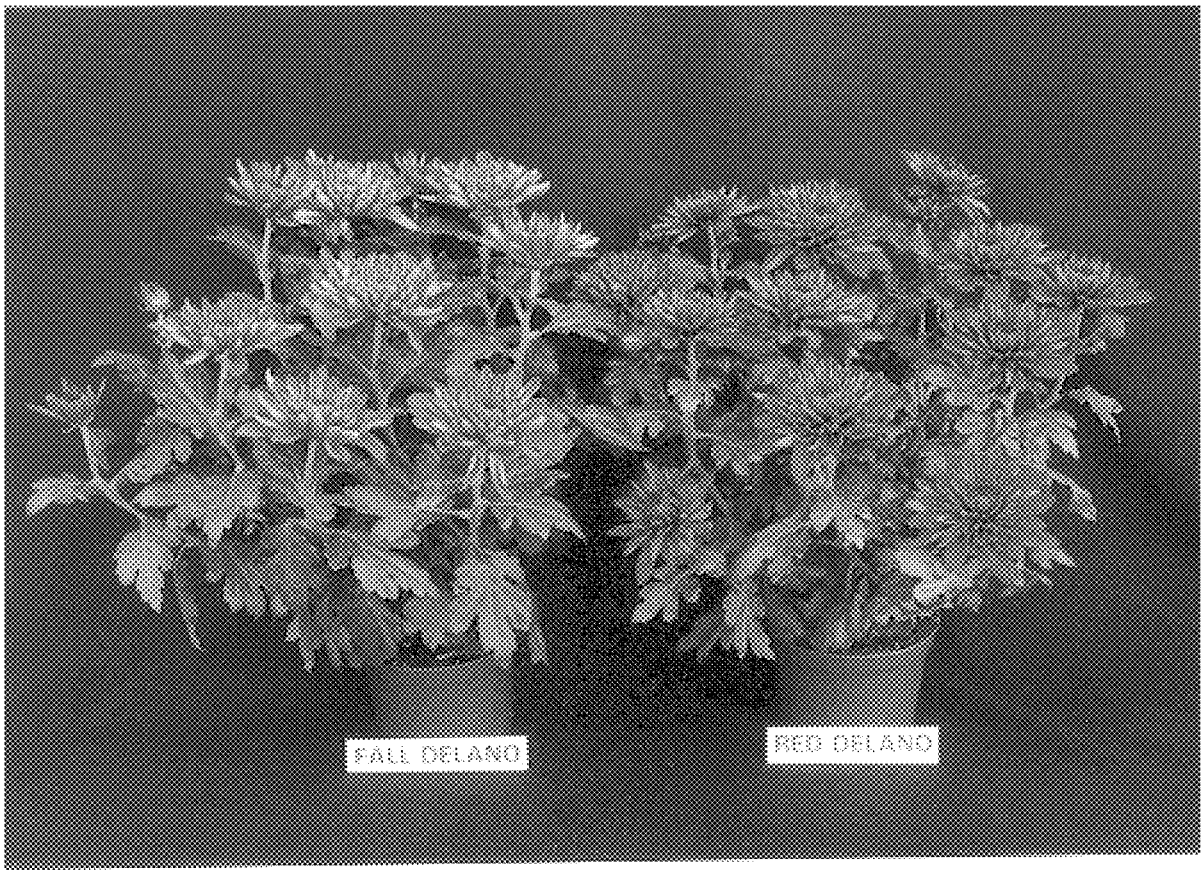
FALL DELANO
RED DELANO